US007049100B2

(12) United States Patent
Santi et al.

(10) Patent No.: US 7,049,100 B2
(45) Date of Patent: May 23, 2006

(54) MULTI-PLASMID METHOD FOR PREPARING LARGE LIBRARIES OF POLYKETIDES AND NON-RIBOSOMAL PEPTIDES

(75) Inventors: Daniel V. Santi, San Francisco, CA (US); Qun Xue, Charlottesville, VA (US); Gary Ashley, Alameda, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 276 days.

(21) Appl. No.: 10/104,417

(22) Filed: Mar. 22, 2002

(65) Prior Publication Data

US 2002/0192756 A1 Dec. 19, 2002

Related U.S. Application Data

(60) Division of application No. 09/548,060, filed on Apr. 12, 2000, now Pat. No. 6,399,789, which is a continuation-in-part of application No. 09/422,073, filed on Oct. 21, 1999, now Pat. No. 6,258,566, which is a continuation of application No. 08/989,332, filed on Dec. 11, 1997, now Pat. No. 6,033,883.

(60) Provisional application No. 60/129,731, filed on Apr. 16, 1999, provisional application No. 60/033,193, filed on Dec. 18, 1996.

(51) Int. Cl.
*C12P 19/62* (2006.01)
*C12N 9/00* (2006.01)

(52) U.S. Cl. .................. 435/76; 435/183; 536/23.2; 536/23.1; 536/23.7

(58) Field of Classification Search .................. 435/76, 435/183
See application file for complete search history.

(56) References Cited

U.S. PATENT DOCUMENTS

| | | | | |
|---|---|---|---|---|
| 5,672,491 | A | 9/1997 | Khosla et al. | 435/148 |
| 5,712,146 | A | 1/1998 | Khosla et al. | 435/252.35 |
| 5,824,513 | A | 10/1998 | Katz et al. | 435/76 |
| 5,830,750 | A | 11/1998 | Khosla et al. | 435/252.35 |
| 5,843,718 | A | 12/1998 | Khosla et al. | 435/69.1 |
| 5,958,672 | A * | 9/1999 | Short | 435/4 |
| 5,962,290 | A | 10/1999 | Khosla et al. | 435/183 |
| 5,998,194 | A | 12/1999 | Summers, Jr. et al. | 435/252.33 |
| 6,004,787 | A | 12/1999 | Katz et al. | 435/183 |
| 6,022,731 | A | 2/2000 | Khosla et al. | 435/252.35 |
| 6,033,883 | A | 3/2000 | Barr et al. | 435/148 |
| 6,060,234 | A | 5/2000 | Katz et al. | 435/4 |
| 6,063,561 | A | 5/2000 | Katz et al. | 435/4 |
| 6,066,721 | A | 5/2000 | Khosla et al. | 536/23.1 |
| 6,080,555 | A | 6/2000 | Khosla et al. | 435/41 |
| 6,200,813 | B1 | 3/2001 | Katz et al. | 435/477 |
| 6,271,255 | B1 | 8/2001 | Leadlay et al. | 514/450 |
| 6,274,560 | B1 | 8/2001 | Khosla et al. | 514/29 |
| 6,403,775 | B1 | 6/2002 | McDaniel | 536/7.2 |

FOREIGN PATENT DOCUMENTS

| | | |
|---|---|---|
| WO | WO 96/40968 | 12/1996 |
| WO | WO 97/02358 | 1/1997 |
| WO | WO 98/01546 | 1/1998 |
| WO | WO 98/01571 | 1/1998 |
| WO | WO 98/49315 | 11/1998 |
| WO | WO 99/05283 | 2/1999 |
| WO | WO 00/24907 | 5/2000 |
| WO | WO 00/26349 | 5/2000 |
| WO | WO 00/31247 | 6/2000 |
| WO | WO 00/52152 | 9/2000 |

OTHER PUBLICATIONS

August et al. (1998). *Chem Biol* 5:69-79.
Betlach M.C. et al. (1998). *Biochemistry* 37(42):14937-14942.
Cortes, et al. (1990). *Nature* 348:176-178.
Donadio, et al. (1991). *Science* 252:675-679.
Graziani E.I. et al. (1998). *Bioorganic & Medicinal Chemistry Letters* 8(22):311703120.
Hutchinson C.R. (1999). *Proc Natl Acad Sci USA* 96(7):3336-3338.
Jacobsen, et al. (1997). *Science* 277:367-369.
Kao, et al. (1996). *Biochemistry* 35:12363-12368.
Kao C.M. et al. (1994). *Science* 265(5171):509-512.
Katz, et al. (1993). *Annu Rev Microbiol* 47:875-912.
Khosla C. et al. (1996). *Trends in Biotechnology* 14(9):335-341.
Liu, et al. (1997). *J Am Chem Soc* 119:10553-10554.
Marahiel M.A. et al. (1997). *Chem Reviews* 97(7):265102673.
Marsden, et al. (1998). *Science* 279:199-202.
McDaniel, et al. (1997). *J Am Soc* 119:4309-4310.
McDaniel, et al. (1999). *Proc Natl Acad Sci USA* 96:1846-1851.
Olano C. et al. (1998). *Mol and Gen Genetics* 259(3):299-308.
Patten, et al. (1997). *Curr Op Biotechnol* 8:724-733.
Quiros et al. (1995). *Chemistry* 270(31):18234-18239.
Ruan X. et al. (1997). *J Bacteriol* 179(20):6416-6425.
Schneider A. et al. (1998). *Mol and Gen Genetics* 257(3):308-318.
Schwecke, et al. (1995). *Proc Natl Acad Sci USA* 92:7839-7843.
Tang L. et al. (2000). *Science* 287(28):640-642.
Tang L. et al. (2000). *Chem & Biol* 7(2):77-84.
Xue Y. et al. (1998). *Proc Natl Acad Sci USA* 95(21):12111-12116.
Xue et al. (1999). 132:45550 Chemical Abstracts.
Xue Q. et al. (1999). *Proc Natl Acad Sci USA* 96(21):11740-11745.

* cited by examiner

*Primary Examiner*—Nashaat T. Nashed
(74) *Attorney, Agent, or Firm*—Morrison & Foerster LLP

(57) ABSTRACT

A multiple-plasmid system for heterologous expression of polyketides facilitates combinatorial biosynthesis. The method can be extended to any modular polyketide synthase (PKS) or non-ribosomal peptide synthase (NRPS) and has the potential to produce thousands of novel natural products, including ones derived from further modification of the PKS or NRPS products by tailoring enzymes.

21 Claims, 9 Drawing Sheets

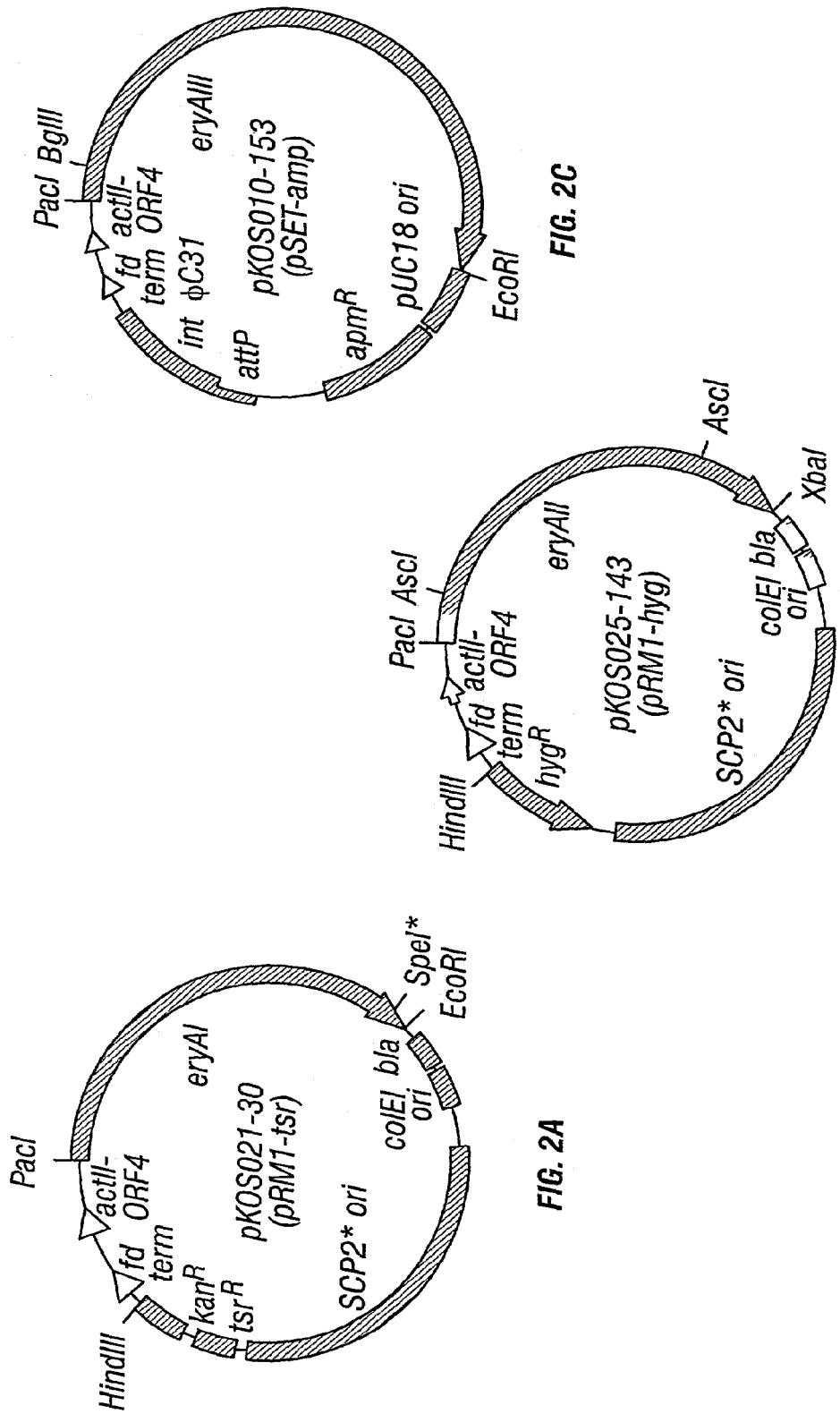

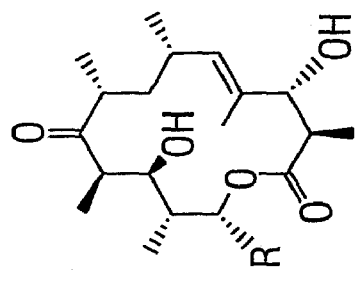
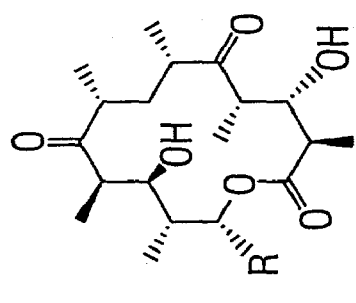
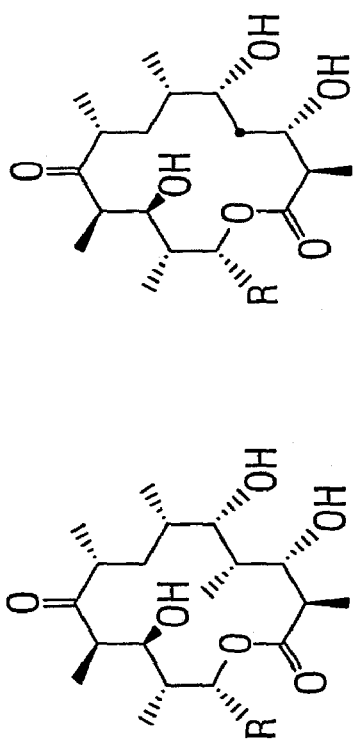
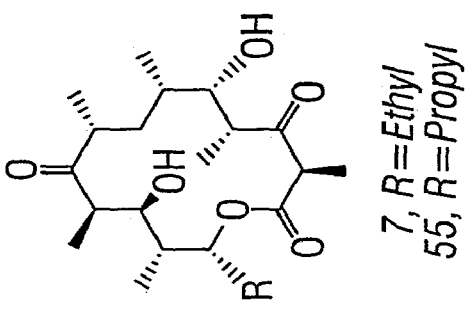
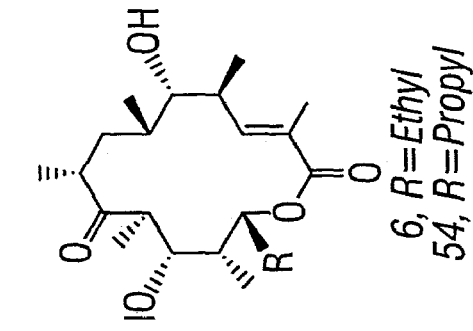
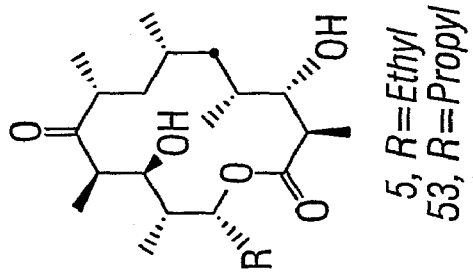
FIG. 3A

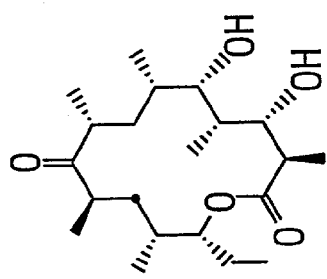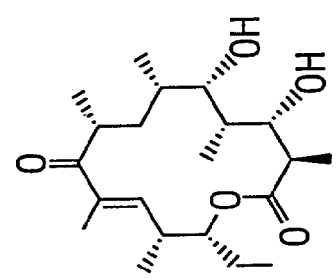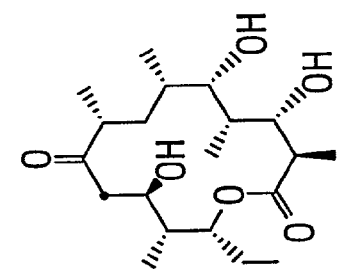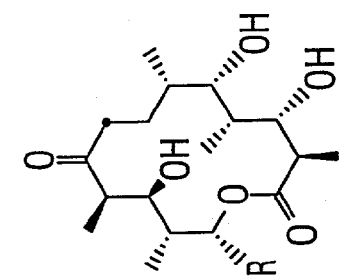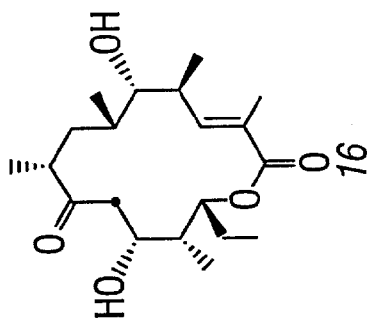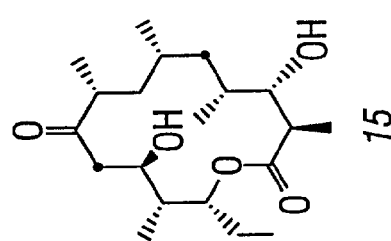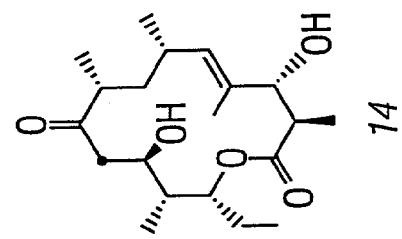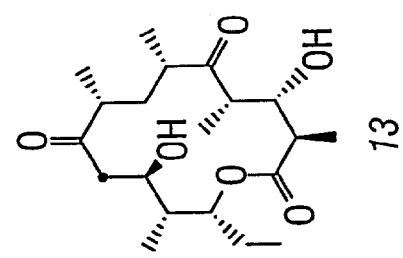
FIG. 3B

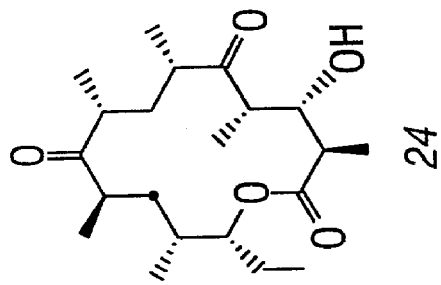
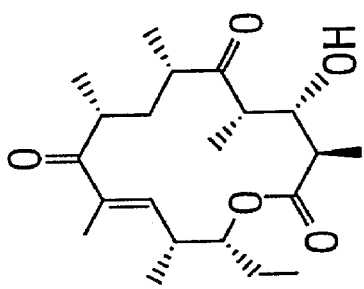
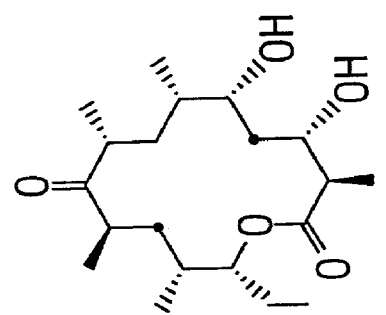
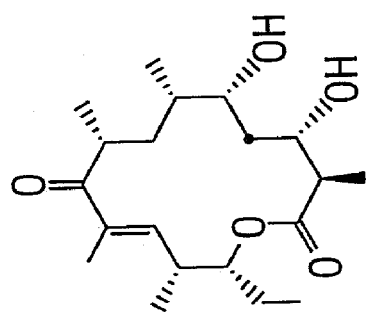
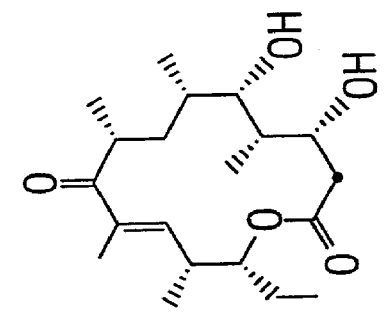
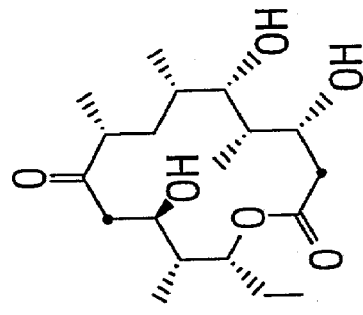
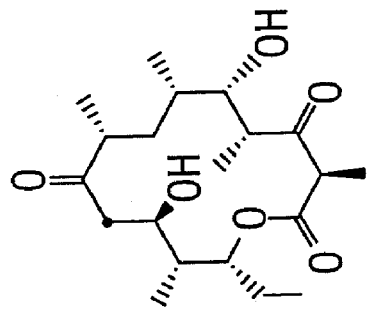
FIG. 3C

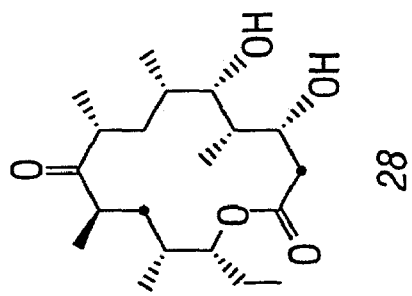
28
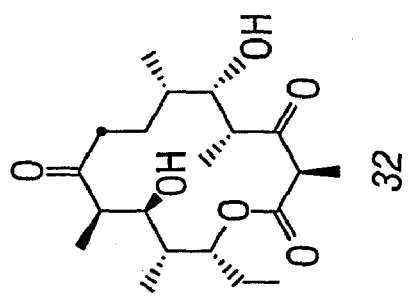
32
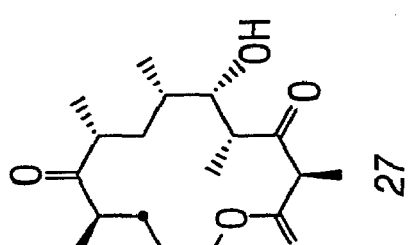
27
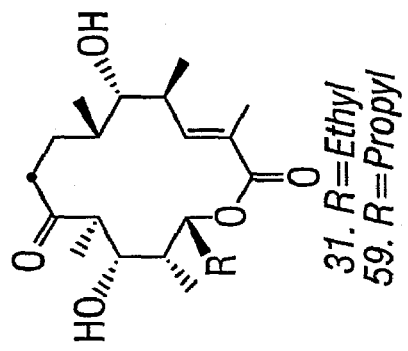
31. R=Ethyl
59. R=Propyl
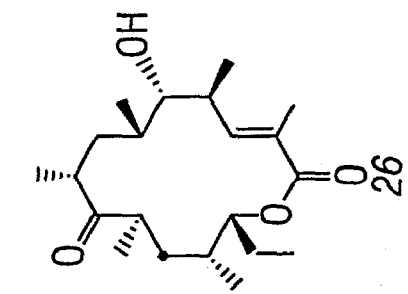
26
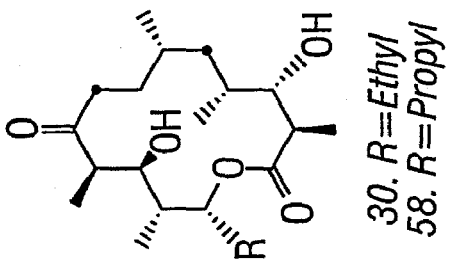
30. R=Ethyl
58. R=Propyl
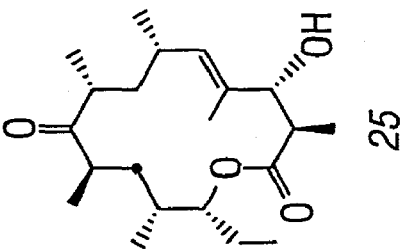
25
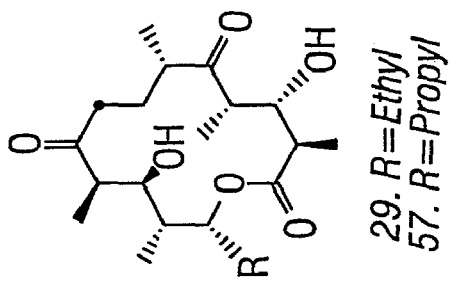
29. R=Ethyl
57. R=Propyl
FIG. 3D

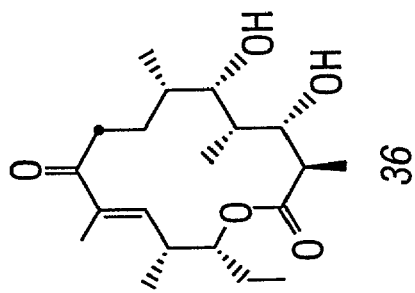
36
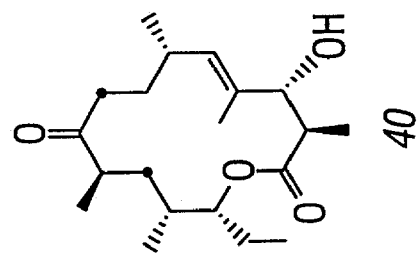
40
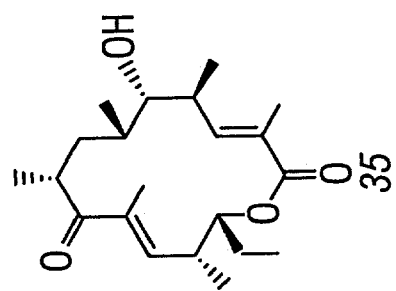
35
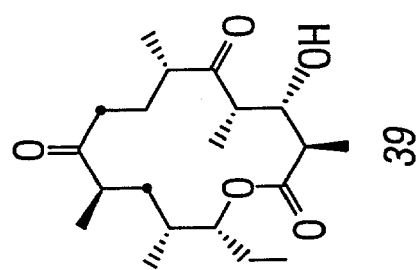
39
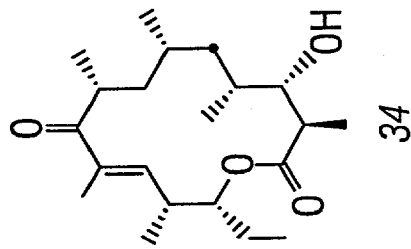
34
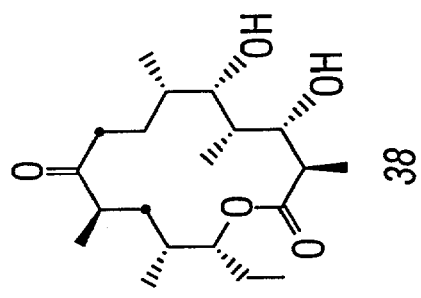
38
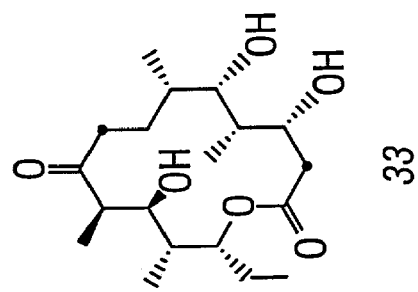
33
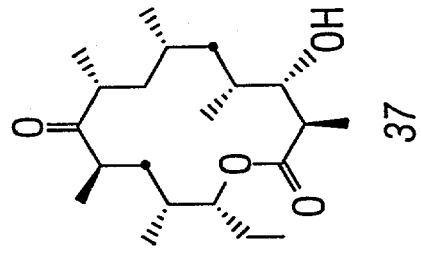
37
FIG. 3E

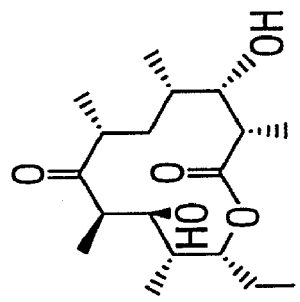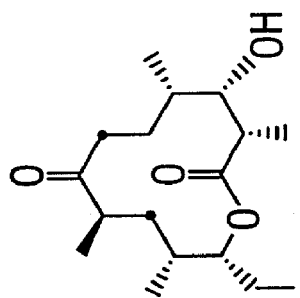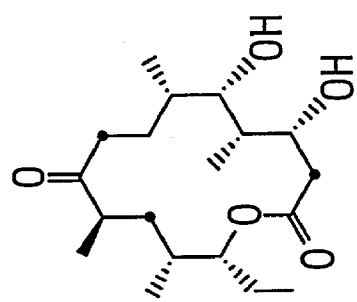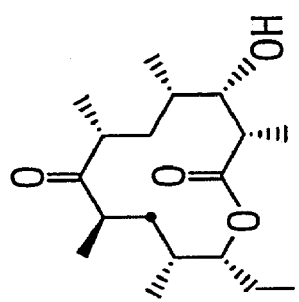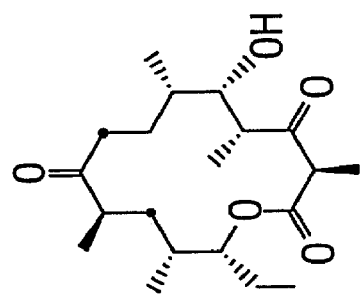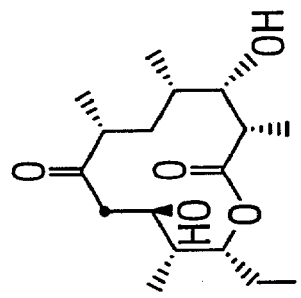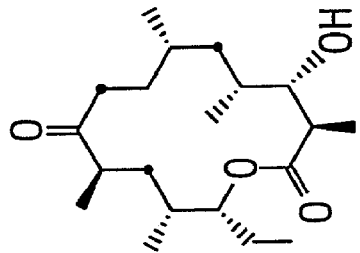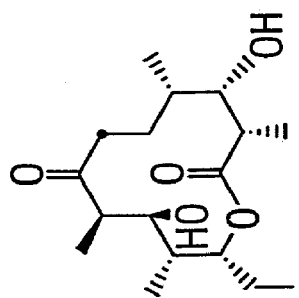
FIG. 3F

MULTI-PLASMID METHOD FOR PREPARING LARGE LIBRARIES OF POLYKETIDES AND NON-RIBOSOMAL PEPTIDES

STATEMENT OF GOVERNMENT INTEREST

This invention was supported in part by SBIR Grant No. GM56575. The United States government has certain rights in this invention.

CROSS-REFERENCE TO RELATED APPLICATIONS

This application claims priority to and is a divisional of U.S. Ser. No. 09/548,060, filed 12 Apr. 2000, now U.S. Pat. No. 6,399,789, which is a continuation-in-part of U.S. Ser. No. 09/422,073, filed 21 Oct. 1999, now U.S. Pat. No. 6,258,566, which is a continuation of U.S. Ser. No. 08/989,332, filed 11 Dec. 1997, now U.S. Pat. No. 6,033,883, which claims priority to U.S. Ser. No. 60/033,193, filed 18 Dec. 1996, now lapsed. U.S. Ser. No. 09/548,060, mentioned above, also claims priority to U.S. provisional application Ser. No. 60/129,731, filed 16 Apr. 1999, now lapsed. Each of the above patent applications is incorporated herein by reference.

FIELD OF THE INVENTION

The present invention provides recombinant DNA compounds and host cells containing novel polyketide synthase (PKS) genes and novel polyketides. The invention relates to the fields of chemistry, medicinal chemistry, human and veterinary medicine, molecular biology, pharmacology, agriculture, and animal husbandry.

BACKGROUND OF THE INVENTION

Polyketides are structurally diverse natural products that include important therapeutic agents used as antibacterials (erythromycin), immunosuppressants (FK506), cholesterol lowering agents (lovastatin), and others (see Katz et al., 1993, Polyketide synthesis: prospects for hybrid antibiotics, *Annu. Rev. Microbiol.* 47: 875–912, incorporated herein by reference). Currently, there are about 7,000 identified polyketides, but this represents only a small fraction of what nature is capable of producing.

DNA sequencing of genes encoding several of the enzymes that produce type 1 modular polyketide synthases (PKSs) has revealed the remarkably logical organization of these multifunctional enzymes (see Cortes et al., 1990, An unusually large multifunctional polypeptide in the erythromycin-producing polyketide synthase of *Saccharopolyspora erythraea*, *Nature* 348: 176–178; Donadio et al., 1991, Modular organization of genes required for complex polyketide biosynthesis, *Science* 252: 675–679; Schwecke et al., 1995, The biosynthetic gene cluster for the polyketide immunosuppressant rapamycin, *Proc. Natl. Acad. Sci. USA* 92: 7839–7843; and August et al., 1998, Biosynthesis of the ansamycin antibiotic rifamycin: deductions from the molecular analysis of the rif biosynthetic gene cluster of *Amycolatopsis mediterranei* S699, *Chem Biol* 5: 69–79, each of which is incorporated herein by reference). The application of innovative combinatorial techniques to this genetic organization has prompted the generation of novel natural products, by adding, deleting, or exchanging domains or entire modules. See U.S. Pat. Nos. 5,672,491; 5,712,146; 5,830,750; 5,843,718; 5,962,290; and 6,022,731, each of which is incorporated herein by reference. It would be advantageous to have a practical combinatorial biosynthesis technology that could achieve and perhaps exceed the diversity of modular polyketide structures thus far revealed in nature.

The known modular PKSs have a linear organization of modules, each of which contains the activities needed for one cycle of polyketide chain elongation, as illustrated for 6-deoxyerythronolide B synthase (DEBS) in FIG. 1A. The minimal module contains a ketosynthase (KS), an acyltransferase (AT), and an acyl carrier protein (ACP) that together catalyze a 2-carbon extension of the chain. The specificity of the AT for either malonyl or an alpha-alkyl malonyl CoA determines which 2-carbon extender is used, and thus the nature of the alkyl substituent at the alpha-carbon of the growing polyketide chain. After each 2-carbon unit condensation, the oxidation state of the beta-carbon is either retained as a ketone, or modified to a hydroxyl, methenyl, or methylene group by the presence a ketoreductase (KR), a KR+ a dehydratase (DH), or a KR+DH+ an enoyl reductase (ER), respectively. In effect, the AT specificity and the composition of catalytic domains within a module serve as a "code" for the structure of each 2-carbon unit. The order of the modules in a PKS specifies the sequence of the distinct 2-carbon units, and the number of modules determines the size of the polyketide chain.

The remarkable structural diversity of polyketides (see O'Hagan, *The Polyketide Metabolites*; Ellis Horwood, Chichester, 1991, incorporated herein by reference) is governed by the combinatorial possibilities of arranging modules containing the various catalytic domains, the sequence and number of modules, and the post-PKS "tailoring enzymes" that accompany the PKS genes. The direct correspondence between the catalytic domains of modules in a PKS and the structure of the resulting biosynthetic product allows rational modification of polyketide structure by genetic engineering.

Over the past several years, examples of modifying each of the elements that code for polyketide structure has been accomplished (see Kao et al., 1996, Evidence for two catalytically independent clusters of active sites in a functional modular polyketide synthase, *Biochemistry* 35: 12363–12368; Liu et al., 1997, Biosynthesis of 2-nor-6-deoxyerythronolide B by rationally designed domain substitution, *J. Am. Chem. Soc.* 119: 10553–10554; McDaniel et al., 1997, Gain-of-function mutagenesis of a modular polyketide synthase, *J. Am. Chem. Soc.* 119: 4309–4310; Marsden et al., 1998, Engineering broader specificity into an antibiotic-producing polyketide synthase, *Science* 279: 199–202; and Jacobsen et al., 1997, Precursor-directed biosynthesis of erythromycin analogs by an engineered polyketide synthase, *Science* 277: 367–369, each of which is incorporated herein by reference).

Recently, a combinatorial library of over 50 novel polyketides was prepared by systematic modification of DEBS, the PKS that produces the macrolide aglycone precursor of erythromycin (see U.S. patent application Ser. No. 09/429,349, filed Oct. 28, 1999; PCT patent application US99/24483, filed 20, Oct. 1999; and McDaniel et al., 1999, Multiple genetic modification of the erythromycin gene cluster to produce a library of novel "unnatural" natural products, *Proc. Natl. Acad. Sci. USA* 96: 1846–1851, each of which is incorporated herein by reference). With a single plasmid containing the eryAI, -AII and -AIII genes encoding the three DEBS subunits, ATs and beta-carbon processing domains were substituted by counterparts from the rapamycin PKS (see Schwecke et al., 1995, supra) that encode alternative substrate specificities and beta-carbon processing activities. The approach used was to develop single "mutations", then sequentially combine the single mutations to produce multiple changes in the PKS. It was observed that when two or more single PKS mutants were functional, there was a high likelihood that combinations would also produce the expected polyketide. Although this strategy provided high assurance that the multiple mutants would be productive, the production of each polyketide required a separate engineering. Thus, if X mutants of eryAI, Y mutants of eryAII, and Z mutants at eryAIII were prepared, X+Y+Z separate experiments were required to produce that same number of polyketides. Clearly, the preparation of very large libraries by this approach is laborious.

Another strategy for preparing large numbers of polyketides is by random digestion-religation leading to "mutagenesis" of the domains or modules of a mixture of PKS genes, including the refinements embodied in the DNA shuffling method (see Patten et al., 1997, Applications of DNA shuffling to pharmaceuticals and vaccines, *Curr. Op. Biotechnol.* 8: 724–733, incorporated herein by reference). The expected low probability of assembling an active PKS by such an approach, however, would demand an extraordinary analytical effort (in the absence of a biological selection) to detect clones that produced polyketides within the much larger number of clones that are non-producers.

There remains a need for practical approaches to create large libraries of polyketides, non-ribosomal peptides, and mixed polyketides/non-ribosomal peptides.

SUMMARY OF THE INVENTION

The present invention provides a method for expressing a polyketide or non-ribosomal peptide in a host cell employing a multiplicity of recombinant vectors, which may be integrative or freely replicating. Each of the multiplicity of vectors encodes a portion of the polyketide synthase or non-ribosomal peptide synthase that produces the polyketide or non-ribosomal peptide. In one embodiment, at least one of the multiplicity of vectors encodes one or more proteins that further modify the polyketide or non-ribosomal peptide produced.

In a preferred embodiment, the vectors replicate in and/or integrate into the chromosome of a *Streptomyces* host cell. Preferred integrating vectors include vectors derived from pSET152 and pSAM2. Preferred replicating vectors include those containing a replicon derived from SCP2* or pJV1.

In another embodiment, the present invention provides novel polyketides. Such novel polyketides include those shown in FIGS. 3A–3F as compound nos. 29–43 and 45–59. Other novel polyketides of the invention include the polyketides obtainable by hydroxylation and/or glycosylation of compounds 29–43 and 45–59. Preferred compounds of the invention include those 14-membered macrolactones with a C-6 and/or C-12 hydroxyl and/or a C-3 and/or C-5 glycosyl, including but not limited to those with a desosaminyl residue at C-5 and a cladinosyl residue at C-3.

These and other embodiments, modes, and aspects of the invention are described in more detail in the following description, the examples, and claims set forth below.

DESCRIPTION OF THE DRAWINGS

FIG. 1A depicts the eryAI–eryAIII genes and proteins as broad arrows oriented in the direction of transcription with the domains in modules 1 to 6 of DEBS1–DEBS3 indicated by the symbols defined herein. The first substrate, propionyl-CoA, is attached to the loading domain ACP and (2S)-2-methylmalonyl-CoA to the module 2 ACP. Then, a decarboxylative condensation between the propionate and methylmalonate takes place followed by reduction of the incipient beta-ketone to form the intermediate shown attached to the ACP of module 2. This intermediate is transferred to the ACP of module 3, and the sequence of reactions is repeated at each of the other modules with or without ketone reduction, dehydration, or double bond reduction to form the linear 21-carbon polyketide attached to the ACP of module 6. The linear polyketide then is cyclized and released as 6-deoxyerythronolide B (6dEB). FIG. 1B depicts replacement of the one or more of the domains in DEBS1, DEBS2, or DEBS3 with one of the three rap (rapamycin) PKS domains or cassettes, or deletion of the KR. This results in the corresponding functional group changes shown at one or more of the positions of 6dEB.

FIGS. 2A–2C show an illustrative three-plasmid expression system for eryA genes. In each vector, the eryA gene is expressed under the control of the upstream actI promoter and actII-ORF4 gene as previously described (see Ziermann et al., 2000, A two-vector system for the production of recombinant polyketides in *Streptomyces, J. Ind Microbiol. & Biotech.* 24: 46–50; and Kao et al., 1994, Engineered biosynthesis of a complete macrolactone in a heterologous host, *Science* 265: 509–512, each of which is incorporated herein by reference). To facilitate construction of the various eryA mutations, a SpeI site (ACTAGT) was introduced at nt 10366–1037 1 of the eryAI ORF by making D3455T and A3456S mutations (see Kao et al., 1995, Manipulation of macrolide ring size by directed mutagenesis of a modular polyketide synthase, *J. Am. Chem. Soc.* 117: 9105–9106, incorporated herein by reference) in pKOS025-179. This change enables insertion of the mutated gene segment between the PacI site and the SpeI site of pKOS025-79. After the replacement of the 6-kb fragment between the AscI sites in eryAII (nt 1213 and nt 7290) with a 6-kb AscI fragment containing a specific AT substitution in an intermediate plasmid, the resulting PacI-XbaI fragment containing the mutant eryAII gene was inserted into pKOS025-143. All eryAIII mutants were constructed by replacing the segment in pKOS010-153 between the unique BglII site at nt 251 and the EcoRI site (nt 9290) that overlaps the stop codon.

FIGS. 3A–3F show structures of macrolactones produced by *Streptomyces lividans* strains containing assorted combinations of three plasmids (FIGS. 2A–2C and Table 1). The positions in 6dEB (1) that are altered correspond to the genetic characteristics of modules 2, 3, 5 and 6 of DEBS, as illustrated in FIG. 1A and FIGS. 2A–2C, and listed in Table 1. Structures 1–40 and 49–56 are 14-membered lactones, and structures 44 to 48 are 12-membered lactones. Compounds 49–59 with the C 13 propyl group were produced by mutational biosynthesis with the eryAI KS1° null allele.

DETAILED DESCRIPTION OF THE INVENTION

The present invention provides methods and reagents for using multiple recombinant DNA vectors to produce polyketides in recombinant host cells. In an illustrative embodiment, a three-plasmid system for heterologous expression of 6-deoxyerythronolide B synthase (DEBS) is provided to facilitate combinatorial biosynthesis of polyketides made by type I modular polyketide synthases (PKSs). The eryA PKS genes encoding the three DEBS subunits were individually cloned into three compatible *Streptomyces* vectors carrying mutually selectable antibiotic resistance markers. A strain of *Streptomyces lividans* transformed with all three plasmids produced 6-deoxyerythronolide B at a level similar to that of a strain transformed with a single plasmid containing all three genes.

The utility of this system in combinatorial biosynthesis was demonstrated through production of a library of modified polyketide macrolactones, using versions of each plasmid constructed to contain defined mutations. Combinations of these vector sets were introduced into *Streptomyces lividans*, resulting in strains producing a wide range of 6-deoxyerythronolide B analogs. This method can be applied to any modular PKS or non-ribosomal peptide synthase (NRPS) and has the potential to produce thousands of novel natural products, including ones derived from further modification of the PKS or NRPS products by tailoring enzymes.

Thus, in one aspect, the present invention provides a method for using multiple (two, three, four, or more) recombinant DNA vectors, each encoding a portion of a PKS, NRPS, or tailoring enzyme, to produce a polyketide or non-ribosomal peptide or a mixed polyketide/non-ribosomal peptide in a host cell. In one embodiment, the vectors in combination encode a naturally occurring PKS or NRPS and the corresponding natural product is produced. In another embodiment, the vectors in combination encode naturally occurring proteins from two or more different naturally occurring PKS or NRPS. In another embodiment, at least one of the vectors encodes a protein not found in nature, having been altered by recombinant DNA methodology to change its structure and function.

In one embodiment, the present invention provides a method for creating a polyketide library that enables the production of large libraries of polyketides while retaining the high probability of obtaining productive clones by combining PKS mutations known to be productive. The principle involves cloning mutants of individual open reading frames (ORFs) of a PKS on separate compatible plasmids, then coexpressing the separate ORFs in a suitable host to produce the PKS. Using this multiple plasmid approach, with X mutants of ORF 1, Y mutants of ORF 2, and Z mutants of ORF 3, for instance, a combinatorial library of X×Y×Z mutants can be achieved expeditiously.

Figure 1A:
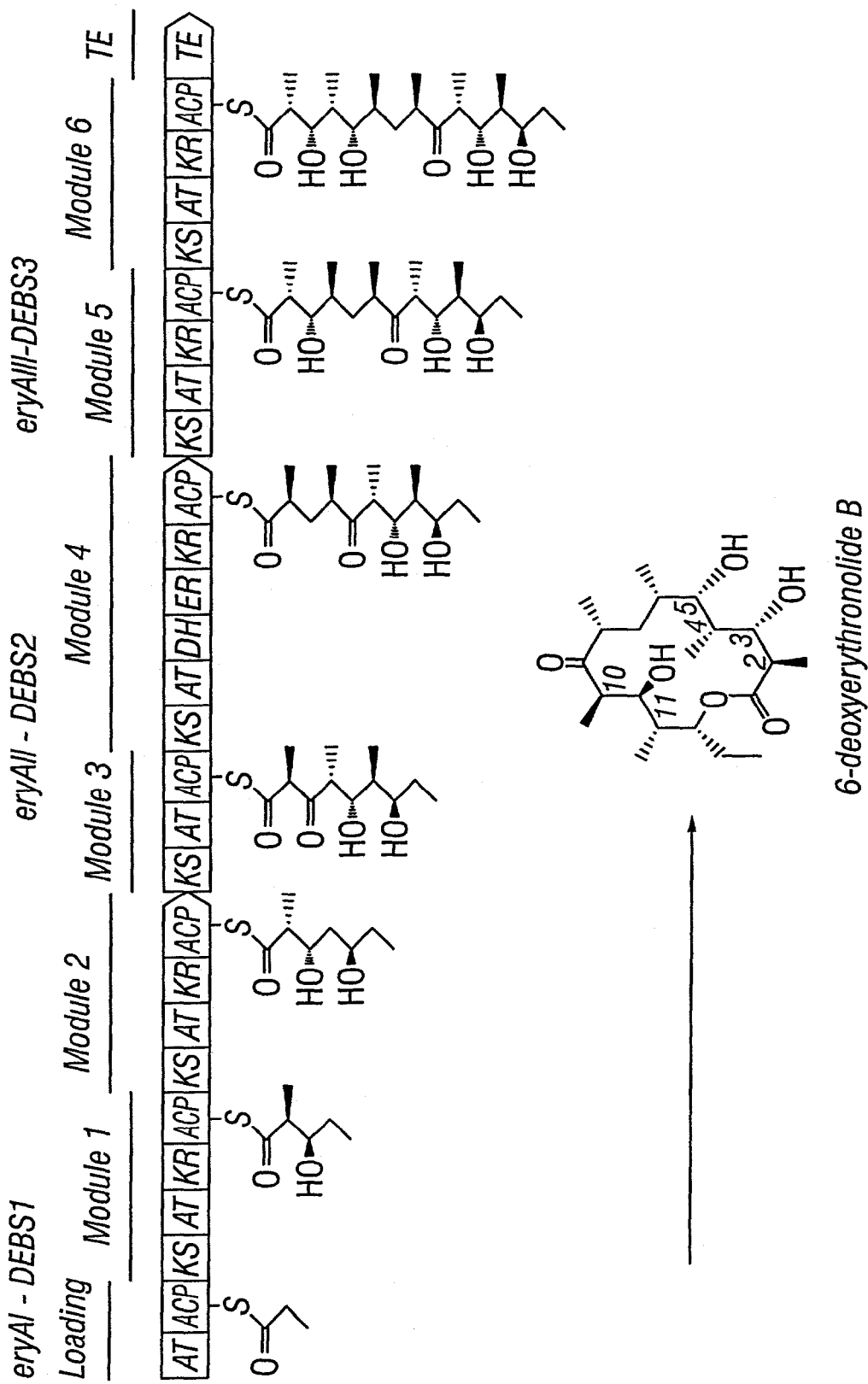
FIG. 1A–1B show wild-type and mutant forms of the eryA genes and DEBS proteins.

DEBS was chosen to illustrate this multiple plasmid approach. The DEBS PKS consists of three >280 kD protein subunits, each containing two modules, that are assembled into the complete PKS complex (see Donadio et al., 1991, supra). With the two possible AT domains and the four possible beta-keto modifications, i.e. eight at each module, therefore 8×8=64 permutations for the two modules are possible in each DEBS subunit. Constructing the mutations in each DEBS ORF separately would require that 64 manipulations be carried out on each gene, or a total of 192 such manipulations. However, by co-transforming a host strain with three plasmids, each bearing the 64 permutations of a different DEBS subunit, one could generate the mutant PKSs necessary to achieve, in theory, a library of 262,144 polyketides ($64^3$), as 6-deoxyerythronolide B (6dEB) analogs (FIG. 1A). In contrast, the same number of mutagenesis experiments performed in a single plasmid system would theoretically yield only 192 polyketides.

The successful implementation of this multiple plasmid strategy requires that the DEBS subunits translated from three different mRNAs faithfully interact to give the active PKS. Some indication that this would be the case was provided by in vitro experiments that showed that reconstitution of the isolated DEBS1–DEBS2 complex with DEBS3 forms a functional PKS (see Pieper et al., 1995, Cell-free synthesis of polyketides by recombinant erythromycin polyketide synthases, *Nature* 378: 263–266, incorporated herein by reference). Further, it was recently demonstrated that coexpression of the three subunits of DEBS from two plasmids produced active PKS in vivo (see Ziermann et al., 2000, supra). The present invention can be applied to any PKS or NRPS, including but not limited to the PKS enzymes, including the KS1 null mutation containing versions, that synthesize oleandolide and megalomicin (see U.S. provisional patent application Ser. No. 60/158,305, filed 8 Oct. 1999, U.S. Pat. No. 6,251,636, filed 28 Oct. 1999, and PCT application No. US99/24478, filed 22 Oct. 1999, each of which is incorporated herein by reference).

The method in one embodiment requires at least three vectors that can be separately introduced into a *Streptomyces* or other suitable host strain and concomitantly express functional PKS subunits. Two such vectors are preferred for such purposes: the autonomously replicating SCP2*-based plasmid pRM1 (see Kao et al., 1994, Engineered biosynthesis of a complete macrolactone in a heterologous host, *Science* 265: 509–512, and U.S. Pat. No. 6,022,731, each of which is incorporated herein by reference) and the integrating bacteriophage phiC31-based plasmid pSET152 (see Bierman et al., 1992, Plasmid cloning vectors for the conjugal transfer of DNA from *Escherichia coli* to *Streptomyces* spp., *Gene* 116:43–49, incorporated herein by reference). Several additional plasmids have been tested as described herein and can be used in accordance with the present invention.

Each of these additional plasmids was tested using constructs that contained identical configurations of an eryA gene downstream of the *Streptomyces coelicolor* actI promoter and actII-ORF4 transcriptional activator as described (see Ziermann et al., 2000, supra). Plasmid pB45, a high copy replicating plasmid possessing the pJV1 origin (see Servin-Gonzalez et al., 1995, Sequence and functional analysis of the *Streptomyces phaechromogenes* plasmid pJV1 reveals a modular organization of *Streptomyces* plasmids that replicate by rolling circle, *Microbiology* 141: 2499–2510, incorporated herein by reference) carrying eryAII was introduced into *S. lividans* harboring eryAI on pRM1 and eryAIII in the pSET152 integration site; less than 0.1 mg/L of 6dEB was produced in this system compared with 50 mg/L for the single plasmid system (see Kao et al., 1994, supra).

The multiple vectors used in the present method can include two or more different vectors that share the same origin of replication. For example, two SCP2*-type plasmids carrying different antibiotic markers can coexist and express PKS subunits in a *Streptomyces* sp., as has been reported using high-copy number plasmids (see Rajgarhia et al., 1997, Minimal *Streptomyces* sp. strain C5 daunorubicin polyketide biosynthesis genes required for akianonic acid biosynthesis, *J. Bacteriol.* 179: 2690–2696, incorporated herein by reference). Co-transformation of *S. lividans* with eryAIII/pSET-apm, eryAI/pRM1-tsr and eryAII/pRM1-hyg (FIG. 2A–2C) yielded a strain that also produced 50 mg/L of 6dEB. Further, after over 24 generations under double antibiotic selection, both replicating plasmids could be rescued by standard procedures with unchanged restriction maps (see Hopwood et al., 1985, *Genetic Manzulation of Streptomyces. A laboratory manual*. John Innes Foundation, Norwich, incorporated herein by reference).

The multiple vectors of the present invention can include two or more different integrating vectors as well. For example, the eryAII gene was cloned into a pSAM2 site-specific integrating plasmid (see Smokvina et al., 1990, Construction of a series of pSAM2-based integrative vectors for use in *Actinomycetes, Gene* 94: 53–59, incorporated herein by reference). Sequential transformation of *Streptomyces lividans* with eryAIII/pSET-apm, eryAII/pSAM-hyg and eryAI/pRM1-tsr provided a strain that produced 40–50 mg/L of 6dEB. A potential advantage of this system over the two-replicating vector system is that it requires one fewer antibiotic, and avoids potential problems in maintaining two plasmids containing the same ori in a *Streptomyces* host (see Baltz, 1997, Molecular genetic approaches to yield improvement in *Actinomycetes, Biotechnology of Antibiotics*, 2nd. Edition: pp. 49–62, incorporated herein by reference). However, as shown herein, the two SCP2*-based plasmids and the pSET-derived vector can also be used.

Thus, the invention can be practiced with a wide variety of expression vectors for use in *Streptomyces*. The replicating expression vectors of the present invention include, for example and without limitation, those that comprise an origin of replication from a low copy number vector, such as SCP2* (see Hopwood et al., *Genetic Manipulation of Streptomyces: A Laboratory manual* (The John Innes Foundation, Norwich, U.K., 1985); Lydiate et al., 1985, *Gene* 35: 223–235; and Kieser and Melton, 1988, *Gene* 65: 83–91, each of which is incorporated herein by reference), SLP1.2 (Thompson et al., 1982, *Gene* 20: 51–62, incorporated herein by reference), and pSG5(ts) (Muth et al., 1989, *Mol. Gen. Genet.* 219: 341–348, and Bierman et al., 1992, *Gene* 116:43–49, each of which is incorporated herein by reference), or a high copy number vector, such as pIJ101 and pJV1 (see Katz et al., 1983, *J. Gen. Microbiol.* 129: 2703–2714; Vara et al., 1989, *J. Bacteriol.* 171: 5782–5781; and Servin-Gonzalez, 1993, *Plasmid* 30: 131–140, each of which is incorporated herein by reference). High copy number vectors are, however, generally not preferred for expression of large genes or multiple genes. For non-replicating and integrating vectors and generally for any vector, it is useful to include at least an *E. coli* origin of replication, such as from pUC, p1P, p1I, and pBR. For phage based vectors, the phage phiC31 and its derivative KC515 can be employed (see Hopwood et al., supra). Also, plasmid pSET152, plasmid pSAM, plasmids pSE101 and pSE211, all of which integrate site-specifically in the chromosomal DNA of *S. lividans*, can be employed for purposes of the present invention.

Moreover, a wide variety of selectable markers can be employed in the *Streptomyces* recombinant expression vectors of the invention. These include antibiotic resistance conferring genes selected from the group consisting of the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes. Alternatively, several polyketides are naturally colored, and this characteristic can provide a built-in marker for identifying cells.

An illustrative library of the present invention was constructed. The library was composed of vectors encoding three single mutations in eryAI (module 2), one in eryAII (module 3), and seven in eryAIII (modules 5 or 6) as well as wild-type ORFs, a KS1 null mutant, and a module 6 deletion, as shown in Table 1, below. To facilitate cloning, vectors were prepared that contained restriction sites that allowed transfer of DNA cassettes from previously prepared mutant eryA genes (see McDaniel et al., 1999, supra, and FIGS. 2A–2C). Fourteen of these expression vectors, comprising the three wild-type and eleven mutant ORFs were constructed by cassette transfers from plasmids previously prepared in the single plasmid system.

TABLE 1

Genotype of the plasmids containing DEBS genes[a]

| Vector: pKOS021 | pKOS025 | pKOS010 | |
|---|---|---|---|
| Gene: eryAI(DEBS1) | eryAII(DEBS2) | eryAIII(DEBS3) | |
| Module: 2 | 3 | 5 | 6 |
| 1. wild-type | | | |
| 2. AT –> [b]rapAT2 | | | |
| 3. KR –> rapDH/KR4 | | | |
| 4. KR –> rapDH/ER/KR1 | | | |
| 5. KS1°° | | | |
| | 6. wild-type | | |
| | 7. AT3 –> rapAT2 | | |
| | | 8. wild-type | |
| | | 9. AT –> rapAT2 | |
| | | 10. KR –> AT/ACP linker | |
| | | 11. KR –> rapDH/KR4 | |
| | | 12. KR –> rapDH/ER/KR1 | |
| | | 13. module 5 + TE[d] | |
| | | | 14. AT –> rapAT2 |
| | | | 15. KR –> AT/ACP linker |
| | | | 16. KR –> rapDH/KR4 |

[a]The plasmids with mutant DEBS genes were constructed by cloning the specified DNA segments into one of the three vectors shown in FIGS. 2A–2C.
[b]The arrow signifies that the wild-type domain was replaced with the one indicated.
[c]The Cys729Ala null allele was created by site-specific mutagenesis.
[d]Module 6 was deleted to fuse its TB to the ACP of module 5.

Figure 1B:
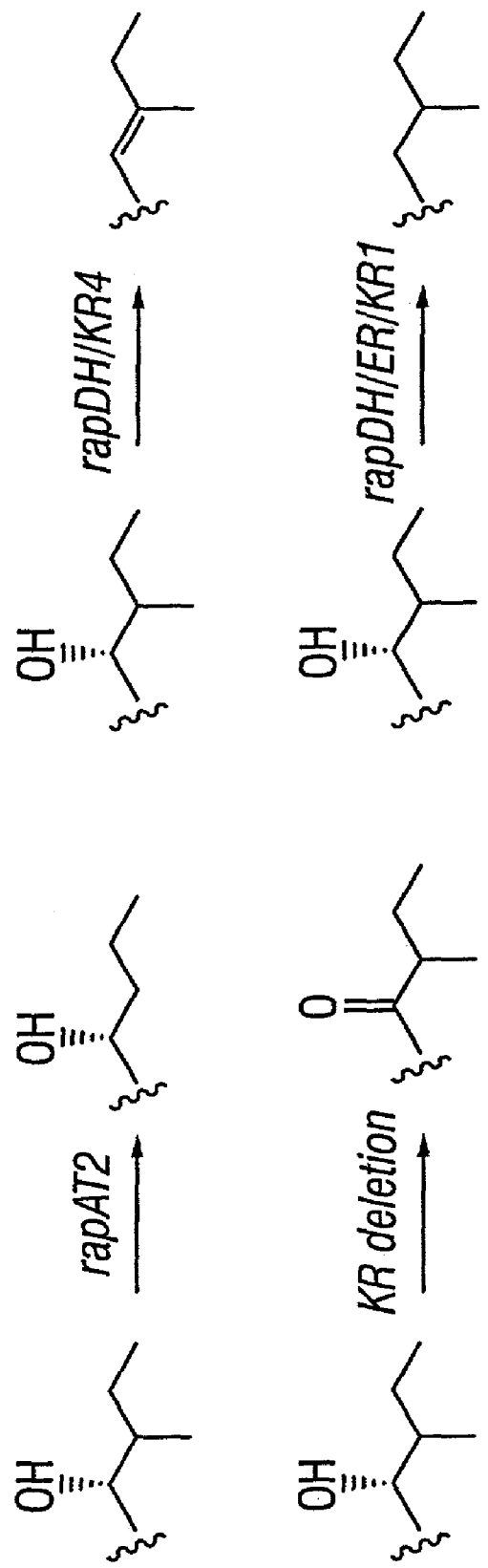

In eryAI, module 2 was modified by replacing the AT by rapAT2 (the AT domain of module 2 of the rapamycin PKS), and the KR by rapDH/KR4 (the DH and KR domains of module 4 of the rapamycin PKS) or rapDH/ER/KR1 (the DH, KR, and ER domains of module 1 of the rapamycin PKS). In eryAII, the AT of module 3 was replaced by rapAT2; in eryAIII, module 5 was modified by replacing the AT by rapAT2, and the KR by rapDH/KR4 or rapDH/ER/KR1 or the AT/ACP linker that eliminates the ery module 5 KR activity. Also, in module 6 the AT was replaced with rapAT2, and the KR by rapDH/KR4 or the AT/ACP linker. The consequence of introducing each of these rapamycin PKS gene cassettes into DEBS is shown in FIG. 1B; at a given alpha-position in the growing polyketide carbon chain, a methyl group can be removed, or a beta-hydroxyl can be changed to a ketone or removed by dehydration to produce a double bond, or the double bond resulting from dehydration can then be reduced to a methylene group.

The approach employed was to first introduce the eight eryAIII variants individually into the pSET integration site of S. lividans, then to cotransform the resulting strains individually with each of four eryAI variants on SCP2*-tsr vectors and two eryAII variants on SCP2*-hyg vectors. Thus, from the 14 vectors prepared, 64 triple transformants were obtained. Recombinant cells were grown under appropriate antibiotic selection, and extracts analyzed for polyketide production by LC/MS. Of the 64 triple transformants, 46 (72%) produced detectable levels of one or more polyketides under the test conditions employed (FIGS. 3A–3F), and 43 different polyketides were produced. These included 6dEB (1), and prodicts arising from 11 single (2–12), 26 double (13–38) and five (39–43) triple mutants of DEBS. Twenty-eight (1–28) of the 43 polyketides produced have been previously prepared using the single-plasmid system. Fifteen (29–43) were novek polyketides readiky identifiable by mass spectra and correspondence to the products expected vased on the cassettes used in the mutagenesis.

In one aspect, the present invention provides these novel polyketides. These novel polyketides can be further modified by tailoring enzymes, including the tailoring enzymes of Saccharopolyspora erythraea. There are a wide variety of diverse organisms that can modify macrolide aglycones to provide compounds with, or that can be readily modified to have, useful activities. For example, Saccharopolyspora erythraea can convert 6-dEB or derivatives thereof to a variety of useful compounds. The erythronolide 6-dEB is converted by the eryf gene product to erythronolide B, which is, in turn, glycosylated by the eryB gene product to obtain 3-O-mycarosylerythronolide B, which contains L-mycarose at C-3. The enzyme eryc gene product then converts this compound to erythromycin D by glycosylation with D-desosamine at C-5. Erythromycin D, therefore, differs from 6-dEB through glycosylation and by the addition of a hydroxyl group at C-6. Erythromycin D can be converted to erythromycin B in a reaction catalyzed by the eryG gene product by methylating the L-mycarose residue at C-3. Erythromycin D is converted to erythromycin C by the addition of a hydroxyl group at C-12 in a reaction catalyzed by the eryK gene product. Erythromycin A is obtained from erythromycin C by methylation of the mycarose residue in a reaction catalyzed by the eryG gene product. The aglycone compounds provided by the present invention, such as, for example, the compounds produced in Streptomyces lividans, can be provided to cultures of S. erythraea and converted to the corresponding derivatives of erythromycins A, B, C, and D. To ensure that only the desired compound is produced, one can use an S. erythraea eryA mutant that is unable to produce 6-dEB but can still carry out the desired conversions (Weber et al., 1985, J. Bacteriol. 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production.

Moreover, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. Thus, Streptomyces venezuelae, which produces picromycin, contains enzymes that can transfer a desosaminyl group to the C-5 hydroxyl and a hydroxyl group to the C-12 position. In addition, S. venezuelae contains a glucosylation activity that glucosylates the 2'-hydroxyl group of the desosamine sugar. This latter modification reduces antibiotic activity, but the glucosyl residue is removed by enzymatic action prior to release of the polyketide from the cell. Another organism, S. narbonensis, contains the same modification enzymes as S. venezuelae, except the C-12 hydroxylase. Thus, the present invention provides the compounds produced by hydroxylation and glycosylation of the macrolide aglycones of the invention by action of the enzymes endogenous to S. narbonensis and S. venezuelae.

Other organisms suitable for making compounds of the invention include Micromonospora megalomicea, which produces megalomicin A. Megalomicin A contains the complete erythromycin C structure, and its biosynthesis also involves the additional formation of megosamine (L-rhodosamine) and its attachment to the C-6 hydroxyl, followed by acylation of the C-3''' and(or) C-4''' hydroxyls as the terminal steps. Other organisms useful in converting the aglycones of the present invention to modified compounds include Streptomyces antibioticus, S. fradiae, and S. thermotolerans. S. antibioticus produces oleandomycin and contains enzymes that hydroxylate the C-6 and C-12 positions, glycosylate the C-3 hydroxyl with oleandrose and the C-5 hydroxyl with desosamine, and form an epoxide at C-8–C-8a. S. fradiae contains enzymes that glycosylate the C-5 hydroxyl with mycaminose and then the 4'-hydroxyl of mycaminose with mycarose, forming a disaccharide. S. thermotolerans contains the same activities as S. fradiae, as well as acylation activities. Thus, the present invention provides the compounds produced by hydroxylation and glycosylation of the macrolide aglycones of the invention by action of the enzymes endogenous to S. antibioticus, S. fradiae, and S. thermotolerans. Moreover, these and other tailoring enzymes can be cloned and incorporated into one or more of the multiple vectors used in accordance with the methods of the present invention to create libraries of modified polyketide compounds.

The resulting compounds can be further modified by synthetic chemistry, i.e., to yield the corresponding ketolides, useful as antibiotics (see, e.g., U.S. provisional patent application Ser. Nos. 60/172,159, filed 17 Dec. 1999; 60/140,175, filed 18 Jun. 1999; 60/172,154, filed 17 Dec. 1999; and 60/129,729, filed 16 Apr. 1999, each of which is incorporated herein by reference), or to yield the corresponding motilides (see U.S. provisional patent application Ser. No. 60/183,338, filed 18 Feb. 2000, inventors G. Ashley et al., incorporated herein by reference).

In 43 of the 46 transformants that produced polyketides in the illustrative library described herein, the isolated polyketides had structures expected of the mutations). However, as observed in corresponding single mutations of the eryA gene in the single-plasmid system, additional products were observed with certain mutations. In most cases, the rapAT2 domain in module 3 recognized and processed both malonyl- and methylmalonyl-CoA and gave the expected 8-nor analogs plus lesser amounts of the 8-methyl analogs. In a few cases, only the 8-methyl analogs were formed. The relaxed-specificity of rapAT2 appears to be module-dependent, because only the expected products were observed with the same rapAT2 sequence at modules 2 or 5 (see Ruan et al., 1997, Acyltransferase domain substitutions in erythromycin polyketide synthase yield novel erythromycin derivatives, *J. Bacteriol.* 179: 6416–25, incorporated herein by reference).

Likewise, when the KR of module 5 was replaced by either the rapDH/KR4 or rapDH/ER/KR1 domains to give the expected 4,5-anhydro and 5-deoxy analogs, respectively, 5-keto analogs were formed in addition to the expected products. This possibly results from transfer of the beta-ketothioester intermediate from KR5 to ACP5 at a rate competitive with its reduction by the heterologous rapKR4 domain. Because aberrant products were not observed with rapDH/KR4 at modules 2 or 6, the non-specificity appears to be module-dependent.

Finally, when the KR of module 2 was replaced with the rapDH/ER/KR1 domain to provide the 11-deoxy analogs, the 10,11-dehydro analogs were often observed as minor but significant products. Here, the intermediate is processed by the heterologous rapKR and DH domains in module 2, but transfer of the 10,11-dehydro intermediate to KS3 must be competitive with the ER-catalyzed reduction. Interestingly, with rapDH/ER/KR1 in module 2 and rapAT2 in module 3, the 10,11-dehydro by-products were not detected. Either the levels produced were too low for detection using the methods employed, or the aberrant dehydro intermediate of module 2 was not processed by module 3 containing the rapAT2 substitution.

Of the 18 transformants that did not produce polyketides at levels detectable in these experiments, two were double mutants and 16 were triple mutants; only one of these mutants was previously prepared in the single-plasmid system where it also failed to produce a detectable polyketide. As previously reported with the single-plasmid system, an increased number of mutations resulted in a decrease in yield to a level undetectable by the analytical method used.

A major advantage of the multiple plasmid system is that once multiple plasmids encoding functional mutants of PKS subunits are available, they can be rapidly combined with one or more additional mutants to expand the library of polyketides. In one example, a single Cys729Ala mutation at the KS 1 domain of DEBS 1 module 1 (see Jacobsen et al., 1997, supra) was prepared, yielding the KS 1 null mutation. The inactive KS 1 prevents propagation of the starter unit and permits introduction of exogenous synthetic diketide thiol esters into positions 12 and 13 of the 14-membered macrolide product. This system was first developed using a single vector, plasmid pJRJ2. Plasmid pJRJ2 encodes the eryAI, eryAII, and eryAIII genes; the eryAI gene contained in the plasmid contains the KS1 null mutation. The KS1 null mutation prevents formation of the 6-deoxyerythronolide B produced by the wild-type gene unless exogenous substrate is provided. Plasmid pJRJ2 and a process for using the plasmid to prepare novel 13-substituted erythromycins are described in PCT publication Nos. 99/03986 and 97/02358 and in U.S. Pat. No. 6,080,555, filed 5 Jul. 1996; U.S. Pat. No. 6,066,721, filed 17 Jul. 1997; and U.S. Pat. No. 6,500, 960, filed 14 May 1999, each of which is incorporated herein by reference. The exogenous substrates provided can ve prepared by the methods and include the compounds descriged in PCT patent poolocation No. PCT/US00/02397 and U.S. Pat. No. 6,492,562, both filed 27 Jan. 2000, by inventors G. Ashley et al., and both of which claim priority to U.S. provisional patent application Ser. No. 60/117,384, filed 27 Jan. 1999, each of which is incorporated herein by reference.

The plasmid encoding the KS1 null allele of eryAI (Table 1) was introduced by co-transformation into *Streptomyces lividans* with the one eryAII mutant and seven eryAIII mutants (Table 1) to provide 16 transformants. Treatment of each of these with a propyl-diketide N-acetylcysteine thioester, following the work of Jacobsen et al., 1997, and the methodology of the patent applications, supra, provided eleven novel 13-propyl polyketide analogs (49–59 FIGS. 3A–3F). Thus, the present invention provides these novel polyketides as well as the compounds resulting from their modification by post-PKS tailoring enzymes (oxidases and glycosylases) or by synthetic chemical methods. To prepare these same PKSs by the single-plasmid system would have required preparation of 16 individual mutants rather than the single KS1 null mutant used in the present method.

In another example, the variants of eryAI and eryAII were used to prepare a small library of 12-membered macrolactones. It was previously shown in the eryA single-plasmid system that omission of module 6, along with fusion of module 5 to the thioesterase domain of DEBS3 (FIG. 1A) results in formation of a 12-membered macrolactone. A truncated eryAIII gene containing module 5-TE (see Kao et al., 1995, Manipulation of macrolide ring size by directed mutagenesis of a modular polyketide synthase, *J. Am. Chem. Soc.* 117: 9105–9106, incorporated herein by reference, and Table 1) was introduced into *Streptomyces lividans*, and the strain transformed with permutations of the four eryAI and two eryAII variants described above. Of the eight 12-membered lactones that could have been produced, five were observed (44–48). Compound 44 results from combining the wild-type eryAI and eryAII genes with the module 5-TE construct, and has previously been prepared in the single-plasmid system; compounds 45–48 are novel products that more than double the number of known 12-membered macrolides. These novel macrolactones constitute an important aspect of the present invention.

Other uses of this multiple plasmid system are as follows. The expression and genetic engineering of very large PKS genes, such as those involved in the biosynthesis of rapamycin (14 modules) or rifamycin (10 modules), is readily achievable by this method. The ORFs for each of the subunits of these and other PKSs, such as the mixed NRPS-PKS for epothilone (see U.S. Pat. No. 6,303,342, filed 19 Nov. 1999, and PCT patent application US99/27438, filed 19 Nov. 1999, each of which is incorporated herein by reference) could be cloned and expressed in the manner used here to greatly simplify genetic manipulations and the structure/function analysis. Thus, in this application of the present method, a naturally occurring polyketide can be expressed in a recombinant host cell.

Similarly, it would be desirable to mix PKS genes from entirely different pathways to facilitate production of heterologous and hybrid PKSs, as precedented by the work of Li et al. involving hybrid erythromycin/picromycin and oleandomycin/picromycinPKS genes (see U.S. Pat. Nos. 6,117, 659, filed 27 May 1999, and 6,251,636, filed 28 Oct. 1999; PCT patent publication No. 99/61599; and PCT patent application No. US99/24478, each of which is incorporated herein by reference). Such work could include extending the carbon chain by the addition of modules.

The PKS libraries generated could be leveraged and expanded by introducing genes for tailoring enzymes that oxidize, hydroxylate, methylate, acylate, glycosylate, or otherwise modify the product of the PKS or a modified polyketide, and genes encoding such enzymes could be employed using an additional vector in the multiple vector system. Various tailoring enzymes from different host organisms could be employed in the same system. Genes for such tailoring enzymes can be obtained as described in the patent applications and publications referenced in the preceding paragraph and elsewhere herein. See also, U.S. Pat. No. 5,998,194, incorporated herein by reference.

Finally, the method should be useful with any system consisting of multimodular proteins, such as the large family of non-ribosomal peptide synthases, which produce many pharmaceutically important compounds such as anti-fungal compounds, anti-cancer compounds, and antibiotics. These important compounds are made by multifunctional synthetases, consisting of complexes of proteins containing between one and eleven modules, comparable to the modular PKSs (see Konz et al., 1999, How do peptide synthase generate structural diversity? *Chem. & Biol.* 6: 39–48, incorporated herein by reference).

The multi-plasmid technology enables the realization of the full potential of modular PKSs and NRPSs, and thus libraries containing a complete repertoire of polyketides and non-ribosomal peptides. The achievement of this objective requires only the construction of a limited number of highly expressing, productive single mutants that will assure adequate polyketide production when the mutations are combined. Because all the elements for producing an extraordinarily large polyketide library are contained within this facile system, there is neither need nor benefit to embark on developing more complicated, less reliable systems to reach the same objective.

The following examples are given for the purpose of illustrating the present invention and shall not be construed as being a limitation on the scope of the invention or claims.

EXAMPLE 1

Construction of Expression Plasmids

In each vector, the eryA gene is expressed under the control of the upstream actI promoter and actII-ORF4 gene as previously described (see U.S. Pat. No. 5,672,491 and Ziermann et al., 2000, supra, both of which are incorporated herein by reference). For testing the high copy replicating plasmid possessing the pJV1 origin, the pB45 based *E. coli* shuttle vector pKOS025-32 was constructed by fusing pB45 with litmus 28 (New England Biolabs) at BglII and PstI sites. Into pKOS025-32 the ca. 14-kb HindIII-XbaI fragment containing the actI promoter and actII-ORF4 gene was inserted followed by the eyAII gene to give pKOS025-35. The configuration of the components in the HindIII-XbaI fragment is shown in FIG. 2B. The same HindIII-XbaI fragment was also cloned into shuttle vector pOSint1/Hygro (see Raynal et al., 1998, Structure of the chromosomal insertion site for pSAM2: functional analysis in *Eseherichia coli Molecular Microbiology* 28: 333–342, incorporated herein by reference) to yield the eryAII/pSAM2-hyg plasmid, pKOS038-67.

EXAMPLE 2

Transfer of Mutation Cassettes into the Three-plasmid System

The plasmids containing eryAI mutations in module 2 were pKOS025-179 (AT2→rapAT2), pKOS038-1 (KR→rapDH/KR4) and pKOS038-3 (KR→rapDH/ER/KR1) and were made as follows. The PacI-SpeI fragments containing the corresponding mutations were transferred into the plasmids described in FIGS. 2A–2C from plasmids pKOS008-41, pKOS015-56 and pKOS015-57, respectively (see McDaniel et al., 1999, supra, and U.S. Pat. No. 6,403,775, filed 28 Oct. 1999, and PCT patent application US99/24483, filed 20 Oct. 1999, each of which are incorporated herein by reference). The plasmids containing the eryAIII mutations in module 5 were pKOS025-1831 (AT→rapAT2), pKOS025-1832 (KR→AT/ACP linker), pKOS025-1833 (KR→rapDH/KR4) and pKOS025-1834 (KR→rapDH/ER/KR1); and in module 6 were pKOS025-1841(KR→rapDH/KR4), pKOS021-106 (KR→AT/ACP linker) and pKOS025-1842 (AT→rapAT2). These were constructed as follows. The BglII-EcoRI fragments containing the corresponding mutations were transferred into the plasmids described in FIGS. 2A–2C from plasmids pKOS006-188, pKOS016-12, pKOS006-178, pKOS026-11b, pKOS011-25, pKOS011-13 and pKOS015-53, respectively (see McDaniel et al., 1999, supra, and U.S. Pat. No. 6,403,775, filed 28 Oct. 1999, and PCT patent application US99/24483, filed 20 Oct. 1999, each of which are incorporated herein by reference). Plasmid pKOS038-20 contains eryAII with the AT3→rapAT2 replacement in module 3 and was made by transferring the mutation from a previously prepared sub-clone pKOS015-28 (see McDaniel et al., 1999, supra, and U.S. Pat. No. 6,403,775, filed 28 Oct. 1999, and PCT patent application US99/24483, filed 20 Oct. 1999, each of which are incorporated herein by reference).

EXAMPLE 3

*Streptomyces* Transformation

*Streptomyces lividans* K4–114 and K4–155 (see U.S. Pat. No. 6,177,262, filed 28 Oct. 1998, and Ziermann et al., 1999, Recombinant polyketide synthesis in *Streptomyces*: engineering of improved host strain, *Bio Techniques* 26: 106–110, both of which are incorporated herein by reference) transformants were prepared according to standard methods (see Hopwood et al., 1985, supra) using apramycin (100 µg/mL), thiostrepton (50 µg/mL), and hygromycin (225 µg/mL) in the R5 protoplast regeneration plates. In the three-plasmid system for which eryAII/pSAM2-hyg replaced eryAII/SCP2*-hyg, *S. lividans* was transformed sequentially with pKOS010-153, pKOS038-67, and pKOS021-30.

EXAMPLE 4

Diketide Feeding

The (2S, 3R)-2-methyl-3-hydroxyhexanoyl-N-acetylcysteamine (NAC) thioester (propyl diketide) was synthesized in accordance with the method described in U.S. provisional patent application Ser. No. 60/117,384, filed 27 Jan. 1999, and U.S. Pat. No. 6,492,562, filed 27 Jan. 2000, by the same inventors and claiming priority to the foregoing application. The *Streptomyces lividans* triple transformants containing the KS1 null allele of eryAI (see Jacobsen et al., 1997, supra, and PCT patent publication Nos. 99/03986 and 97/02358, each of which is incorporated herein by reference) were cultured in 5 mL of R5 medium at 30° C. for 6 days under appropriate antibiotic selection. On day 4 of the incubation, 300 µL of diketide solution (4.7 mg/mL in 10% DMSO) and 50 µL of pentanoic acid (2.5 mg/mL) were added to the culture.

EXAMPLE 5

Production and Analysis of Polyketide Analogs

The *Streptomyces lividans* triple transformants were cultured in 5 mL of R5 medium (see Hopwood et al., 1985, supra) at 30° C. for 6 days under appropriate antibiotic selection. The cultured solution was extracted with 2×5 mL of ethyl acetate and the organic layers were combined and concentrated. A 50 μL aliquot of the concentrates was analyzed by HPLC on a reverse phase $C_{18}$ column (4.6 mm×15 cm, Beckman, Fullerton, Calif.) using a PE SCIEX API100 LC/MS based detector (Perkin-Elmer, Foster City, Calif.). Quantitative determination of polyketide yield was made with evaporative light scattering detection (Analtec model 500 ELSD, Deerfield, Ill.). The polyketides were identified by their mass spectrum and correspondence to the products expected or to known standards. Under the ionization conditions used, 6dEB and its analogs generate signature dehydration patterns. The yield of the 13-ethyl 6dEB analogs varied from 7 mg/L to less than 0.1 mg/L and the 13-propyl analogs were produced in a range of 0.2 to 20 mg/L. The yields of the 12-membered lactones were not determined.

The invention having now been described by way of written description and examples, those of skill in the art will recognize that the invention can be practiced in a variety of embodiments and that the foregoing description and examples are for purposes of illustration and not limitation of the following claims.

The invention claimed is:

1. A method for expressing a modular polyketide synthase (PKS) which produces a polyketide or a non-ribosomal peptide synthase (NRPS) that produces a non-ribosomal peptide (NRP) in a host cell comprising:
   (a) introducing a vector selected from a library of recombinant vectors into a host cell; (i) wherein the host cell further comprises an additional vector or vectors; which in conjunction with the selected vector is capable of producing the polyketide or NRP; or (ii) wherein additional vector or vectors are introduced into the host cell to allow the production of polyketide or NRP; and
   (b) culturing the host cell into which the vector or vectors have been introduced under conditions such that said PKS or NRPS is expressed;
   wherein each of said vectors encodes an open reading frame (ORF) of the PKS or NRPS; wherein said library of recombinant vectors comprises (i) a recombinant vector encoding a first functional mutant ORF and (ii) a recombinant vector encoding a second functional mutant ORF of a wild-type ORF; and wherein each of said vectors may be integrative or freely replicating.

2. The method of claim 1, wherein said vectors encode a modular PKS.

3. The method of claim 2, wherein said PKS is selected from the group consisting of 6-deoxyerythronolide B synthase (DEBS), oleandolide PKS, picromycin PKS, epothilone PKS, and megalomicin PKS.

4. The method of claim 1, wherein at least one vector encoding a protein that glycosylates the polyketide or NRP produced by said PKS or NRPS is further introduced to said host cell.

5. The method of claim 1, wherein at least one of said vectors replicates extrachromosomally in said host cell.

6. The method of claim 1, wherein at least one of said vectors integrates into the chromosome of said host cell.

7. The method of claim 1, wherein said host cell is a *Streptomyces* host cell.

8. The method of claim 1, where additional vector or vectors are introduced into the cell.

9. The method of claim 1, wherein the additional vector or vectors are selected from the library of recombinant vectors.

10. A method for producing a polyketide or an NRP in a host cell comprising:
    (a) introducing a vector selected from a library of recombinant vectors into a host cell; (i) wherein the host cell further comprises an additional vector or vectors; which in conjunction with the selected vector is capable of producing the polyketide or NRP; or (ii) wherein additional vector or vectors are introduced into the host cell to allow the production of polyketide or NRP; and
    (b) culturing the host cell into which the vector or vectors have been introduced under conditions such that said polyketide or NRP is produced;
    wherein each of said vectors encodes a subunit of a modular PKS or NRPS; wherein said library of recombinant vectors comprises (i) a recombinant vector encoding a first functional mutant subunit and (ii) a recombinant vector encoding a second functional mutant subunit or a wild-type subunit; and wherein each of said vectors may be integrative or freely replicating.

11. The method of claim 10, wherein said modular PKS is selected from the group consisting of DEBS, oleandolide PKS, picromycin PKS, epothilone PKS, and megalomicin PKS.

12. The method of claim 10, wherein at least one recombinant vector encoding a protein that glycosylates the polyketide or peptide produced by the modular PKS or NRPS is further introduced to said host cell.

13. The method of claim 10, wherein at least one of said recombinant vector replicates extrachromosomally in said host cell.

14. The method of claim 10, wherein at least one of said recombinant vectors integrates into the chromosome of said host cell.

15. The method of claim 10, wherein said host cell is a *Streptomyces* host cell.

16. The method of claim 15, wherein said host cell is a *Streptomyces lividans* host cell.

17. The method of claim 10, wherein said PKS is DEBS, wherein said subunit is eryAI and said first functional mutant is AT2→rapAT2, KR2→rapDH/KR4, KR2→rapDH/ER/KR1 or KS1°.

18. The method of claim 10, wherein said PKS is DEBS, wherein said subunit is eryAII and said first functional mutant is AT3→rapAT2.

19. The method of claim 10, wherein said PKS is DEBS, wherein said subunit is eryAIII and said first functional mutant is AT5→rapAT2, KR5→AT/ACP linker, KR5→rapDH/KR4, KR5→rapDH/ER/KR1, module 5+TE, AT6→rapAT2, KR6→AT/ACP linker or KR6→rapDH/KR4.

20. The methods of claim 1, where additional vector or vectors are introduced into the cell.

21. The method of claim 10, wherein the additional vector or vectors are selected from the library of recombinant vectors.

* * * * *